US00PP16637P2

(12) United States Plant Patent
Bernuetz

(10) Patent No.: US PP16,637 P2
(45) Date of Patent: Jun. 13, 2006

(54) ***ARGYRANTHEMUM* PLANT NAMED 'OHMADSANT'**

(50) Latin Name: *Argryranthemum×hybrida*
Varietal Denomination: Ohmadsant

(75) Inventor: Andrew Bernuetz, Silverdale (AU)

(73) Assignee: Bonza Botanicals Pty., Ltd., Sydney (AU)

( * ) Notice: Subject to any disclaimer, the term of this patent is extended or adjusted under 35 U.S.C. 154(b) by 96 days.

(21) Appl. No.: 11/011,534

(22) Filed: Dec. 13, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
(74) *Attorney, Agent, or Firm*—Buchanan Ingersoll PC

(57) ABSTRACT

A new and distinct cultivar of *Argyranthemum* plant named 'Ohmadsant' characterized by its semi-double inflorescence form with red/purple-colored ray florets and orange/red-colored disc florets, freely branching character, dark green-colored foliage, and compact and upright growth habit.

1 Drawing Sheet

Latin name of the genus and species of plant claimed: *Argyranthemum×hybrida.*
Variety denomination: 'Ohmadsant'.

BACKGROUND OF THE INVENTION

The present invention relates to a new and distinct cultivar of *Argyranthemum* plant botanically known as *Argyranthemum×hybrida,* and hereinafter referred to by the cultivar name 'Ohmadsant'.

The new *Argyranthemum* originated in a controlled breeding program in Winmalee, New South Wales, Australia during 2001. The objective of the breeding program was the development of *Argyranthemum* cultivars that are freely branching, have a compact and upright growth habit, are freely flowering, and have unique flower coloration.

The female parent of the new cultivar was 'Suparosa', U.S. Plant Pat. No. 13,775, which exhibits red purple-colored flowers, medium green-colored foliage, and compact growth habit. The male parent of the new cultivar was 'Supalight', U.S. Plant Pat. No. 14,128, which exhibits red purple-colored flowers, dark green-colored foliage, and compact growth habit. Seed from the above stated cross was germinated and grown to maturity. One plant within the progeny was discovered and selected by the inventor during June 2002 in a controlled environment at Winmalee, New South Wales, Australia.

Asexual reproduction of the new cultivar by terminal stem cuttings since June 2002 at Winmalee, New South Wales, Australia and West Chicago, Ill. has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Ohmadsant' as a new and distinct cultivar of *Argyranthemum* plant:

1. Single inflorescence form with red/purple-colored ray florets and orange/red-colored disc florets.
2. Dark green-colored foliage.

3. Freely branching character.
4. Compact and upright growth habit.

Plants of the new cultivar differ from plants of the female parent primarily in flower color and from the male parent primarily in flower color. For instance, the ray florets of each of the parental cultivars are white at the base, unlike those of the new cultivar.

Plants of the new cultivar are similar to the cultivar OHAR01240, U.S. Plant patent application No. 15,634. However, in side-by-side comparisons, carried out at West Chicago Ill., plants of the new cultivar differed from plants of 'OHAR01240' in the following characteristics:

1. Plants of the new cultivar have smaller, thinner leaves than plants of 'OHAR01240'.
2. Plants of the new cultivar have smaller inflorescences than plants of 'OHAR01240'.
3. Plants of the new cultivar have darker-colored ray florets than plants of 'OHAR01240'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which more accurately describe the colors of the new cultivar. The plants were grown in 10 cm pots for 13 weeks in a greenhouse at West Chicago, Ill.

DETAILED BOTANICAL DESCRIPTION

Figure 1:
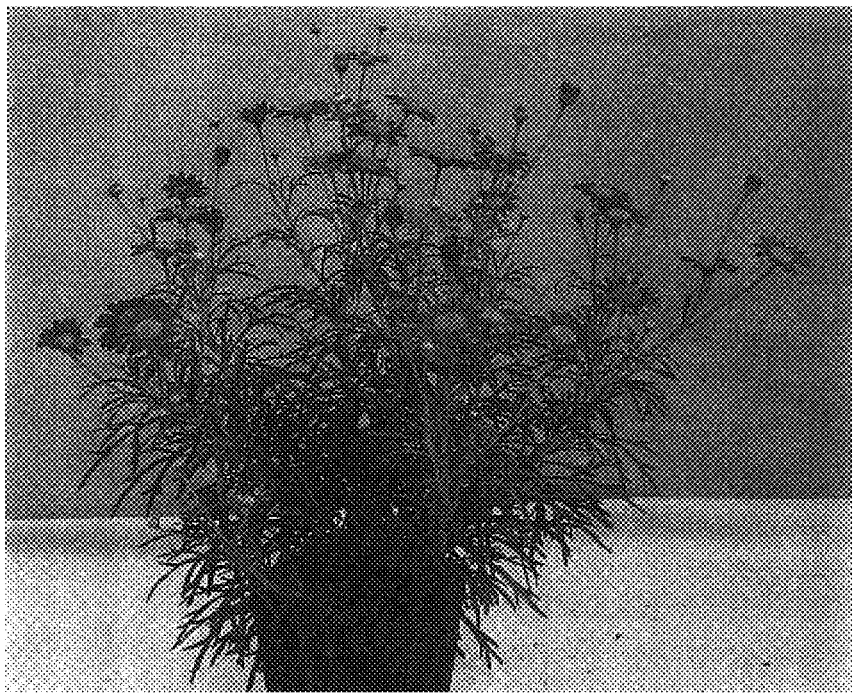
FIG. 1 illustrates a side view of the overall growth and flowering habit of the new cultivar with one plant per pot.
Figure 2:
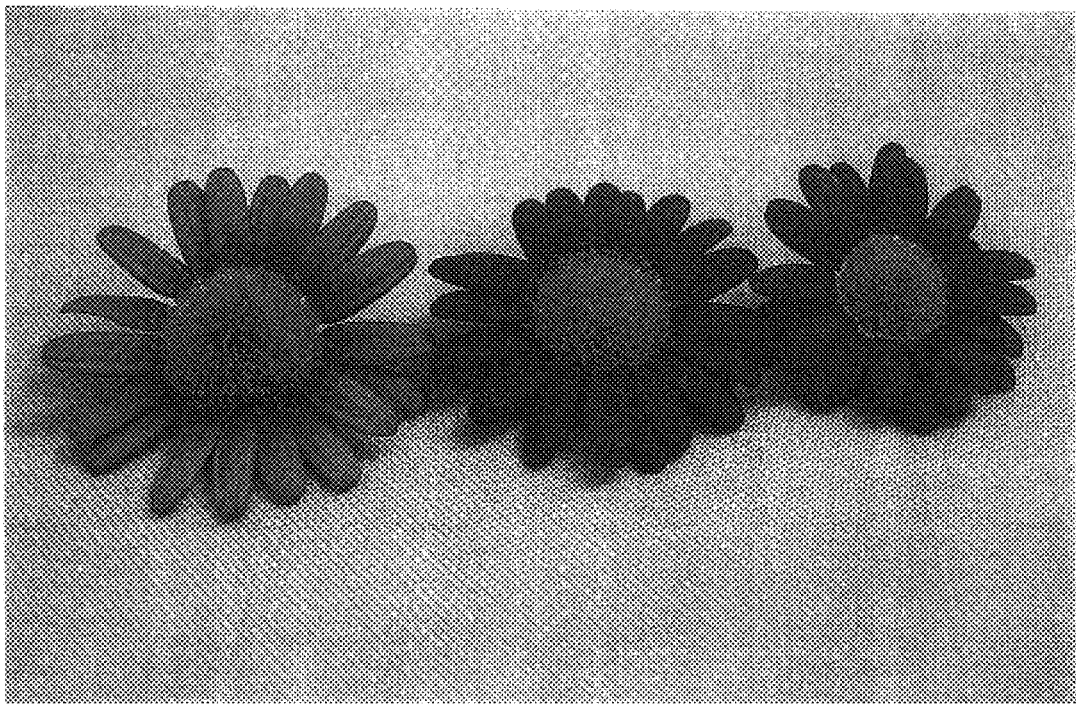
FIG. 2 illustrates a close-up view of individual flowers of the new cultivar showing the change in color as the disc and ray florets mature.

The new cultivar has not been observed under all possible environmental conditions to date. Accordingly, it is possible that the phenotype may vary somewhat with variations in the environment, such as temperature, light intensity, and day length without, however, any variance in genotype The chart used in the identification of colors described herein is The R.H.S. Colour Chart of The Royal Horticultural Society, London, England, 2001 edition, except where color terms of ordinary significance are used. The color values were determined on Sep. 22, 2004 between 1:00 and 3:00 p.m. under natural light conditions.

The following descriptions and measurements describe plants produced from cuttings from stock plants and grown at West Chicago, Ill. in a double polycarbonate-covered greenhouse under conditions comparable to those used in commercial practice. The plants were grown in 10 cm pots for 13 weeks while utilizing a soilless growth medium. Greenhouse temperatures were maintained at approximately 65°–78° F. (18°–25° C.) during the day and approximately 50°–60° F. (10°–15° C.) during the night. Greenhouse light levels were maintained at 6,000 to 9,000 footcandles during the day.

Botanical classification: *Argyranthemum×hybrida* cultivar Ohmadsant.

Parentage:

*Male parent.*—'Supalight', U.S. Plant Pat. No. 14,128.

*Female parent.*—'Suparosa', U.S. Plant Pat. No. 13,775.

Propagation:

*Type cutting.*—Terminal stem.

*Time to initiate roots.*—Approximately 6 to 8 days.

*Time to produce a rooted cutting.*—Approximately 21 to 28 days.

*Root description.*—Fibrous.

*Rooting habit.*—Freely branching.

Plant description:

*Crop time.*—Approximately 6 to 9 weeks from a rooted cutting in a 10 cm pot.

*Growth habit.*—Compact, freely branching. One or two pinches improve basal branching.

*Form.*—Upright, mounded.

*Size.*—Height: Approximately 31.6 cm from soil level to top of plant plane. Width (area of spread) — Approximately 33.7 cm.

*Branch.*—Quantity per plant: Approximately 8. Strength: Strong. Length from soil level to base of peduncle: Approximately 19 cm. Diameter: Approximately 3.2 mm. Texture: Glabrous. Color: 145A. Internode length at middle of branch: Approximately 6.6 mm.

*Foliage.*—Quantity of leaves per branch: Approximately 25. Fragrance: Slight. Type: Simple. Arrangement: Alternate. Aspect: At an acute angle to the stem. Shape: Pinnatified. Apex: Acute. Base: Attenuate, decurrent. Margin: Entire. Venation pattern: Pinnate. Length: Approximately 5.3 cm. Width: Approximately 4.4 cm. Texture: Upper and lower surfaces are glabrous. Color of mature foliage: Upper surface: Darker than 146A with venation of 144B. Lower surface: 146A with venation of 144B.

Flowering description:

*Flowering habit.*—Freely flowering under outdoor growing conditions with substantially continuous blooming from spring through autumn and year round in greenhouse environment.

Inflorescence description:

*Appearance.*—Single composite form. Persistent. Fragrance: None. Shape: Round. Aspect: Facing upward or outward. Disc and ray florets develop acropetally on a capitulum.

*Quantity of flowers and buds per lateral branch.*—Approximately 6 flowers and 4 buds.

*Size.*—Diameter: Approximately 3.3 cm. Depth: Approximately 8.8 mm.

*Lastingness of inflorescence.*—Approximately 7–10 days.

*Bud.*—Rate of opening: Generally it takes 3–6 days for buds to progress from first color to fully open flowers. Shape: Ovoid. Diameter: Approximately 6.4 mm. Depth: Approximately 5.1 mm. Color: 59B.

*Ray florets.*—Quantity per inflorescence: Approximately 13, arranged in a single whorl. Aspect: Flat to slightly concave. Arrangement: Very slightly overlapping. Shape: Ligulate. Margin: Entire. Apex: Emarginate. Base: Attenuate and fused to form tube. Length: Approximately 1.1 cm. Width: Approximately 4.3 mm. Texture: Glabrous and ribbed. Color of ray florets when first open: Upper surface: Closest to 61B. Lower surface: 60C with ribs of 60B. Color of mature ray floret: Upper surface: 70D at apex, 60C at base. Lower surface: 186B. Ray floret color fades to 185D with age.

*Disc.*—Diameter: Approximately 1.1 cm. Depth: Approximately 6 mm.

*Receptacle.*—Shape: Cone. Diameter at base: Approximately 2.2 mm. Depth: Approximately 4 mm. Color: 146C.

*Disc florets.*—Quantity per inflorescence: Approximately 161. Shape: Tubular with five lobes each having an acute apex. Margin: Entire. Length: Approximately 5 mm. Diameter at apex: Approximately 1 mm. Diameter at base: Approximately 0.7 mm. Texture: Glandular. Color: Immature: Closest to 187B. Color: Mature: N34A. Gland color: Colorless and transparent. Calyx: Shape: Tubular. Length: Approximately 2 mm. Diameter: Approximately 1 mm. Texture: Glabrous. Color: Colorless, translucent.

*Phyllaries.*—Quantity per inflorescence: Approximately 16. Arrangement: Imbricate, arranged in several rows. Shape: Ovate. Apex: Acute. Base: Truncate. Margin: Entire. Length: Approximately 4 mm. Width: Approximately 2 mm. Texture: Glabrous, papery along edges. Color of upper surface: Closest to 145C. Color of lower surface: Closest to 145D.

*Peduncle.*—Strength: Strong. Aspect: At an acute angle to the stem. Length: Approximately 3.9 cm. Diameter: Approximately 0.7 mm. Texture: Glabrous. Color: 144A.

*Reproductive organs.*—Androecium: Present on disc florets only. Stamens: 5, fused around style. Anther length: 1 mm. Anther color: 22A. Amount of pollen: None observed. Gynoecium: Present on ray and disc florets. There is one pistil per floret. Pistil length: 4 mm. Stigma shape: Two parted. Stigma length: 1 mm. Stigma color: 14A. Style length: 2.5 mm. Style color: 144D. Ovary diameter: 0.5 mm. Ovary color: 144C.

Seed and fruit production: Neither seed nor fruit production has been observed.

Disease and pest resistance: Resistance to pathogens and pests common to *Argyranthemum* has not been observed.

What is claimed is:

1. A new and distinct cultivar of *Argyranthemum* plant named 'Ohmadsant', substantially as herein shown and described.

* * * * *